United States Patent [19]

Applegate

[11] 4,201,203

[45] May 6, 1980

[54] KNEE BRACE

[75] Inventor: Leslie T. Applegate, Cincinnati, Ohio

[73] Assignee: Surgical Appliance Industries, Inc., Cincinnati, Ohio

[21] Appl. No.: 919,378

[22] Filed: Jun. 26, 1978

[51] Int. Cl.² ............................................. A61F 3/00
[52] U.S. Cl. ..................................... 128/80 C; 2/24
[58] Field of Search ............. 128/80 C, 165, DIG. 15, 128/87 R; 2/22, 24

[56] References Cited

U.S. PATENT DOCUMENTS

| | | | |
|---|---|---|---|
| 3,046,981 | 7/1962 | Biggs, Jr. et al. | 128/80 C |
| 3,387,305 | 6/1968 | Shafer | 128/80 C X |
| 3,945,046 | 3/1976 | Stromgren | 128/165 X |
| 4,116,236 | 9/1978 | Albert | 128/80 C |

*Primary Examiner*—John D. Yasko

*Attorney, Agent, or Firm*—Wood, Herron & Evans

[57] ABSTRACT

A knee brace is disclosed including an elastic sleeve configured to snugly embrace the user's knee region. The sleeve is provided with an opening in the front for the patella. A drawstring slidable in a two-way stretch elastic casing stitched to the margin of the opening facilitates adjustment of the circumference of the opening to snugly engage patellas of different sizes and/or shapes. Lateral pads disposed on either side of the patella opening and a vertical pad disposed above the opening are also included. Adjustable fasteners between the pads and the sleeve interior permit the horizontal spacing between the lateral pads and the center of the kneecap opening and the vertical spacing between the upper pad and the center of the kneecap opening to be varied to accommodate different sized patellas.

13 Claims, 7 Drawing Figures

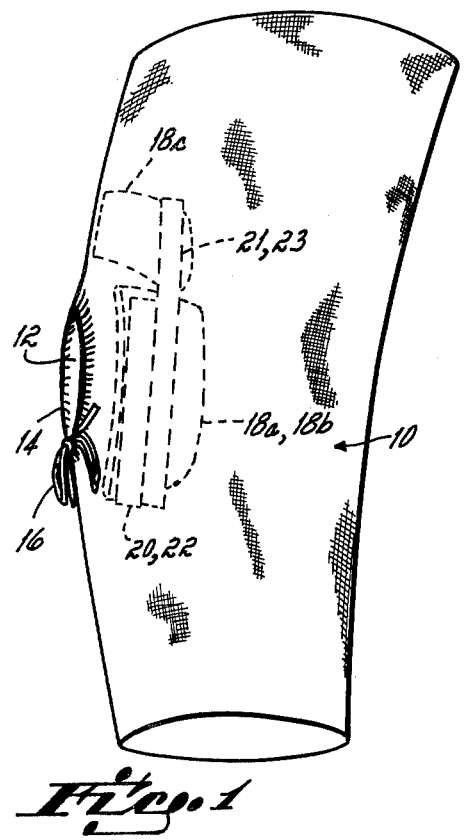
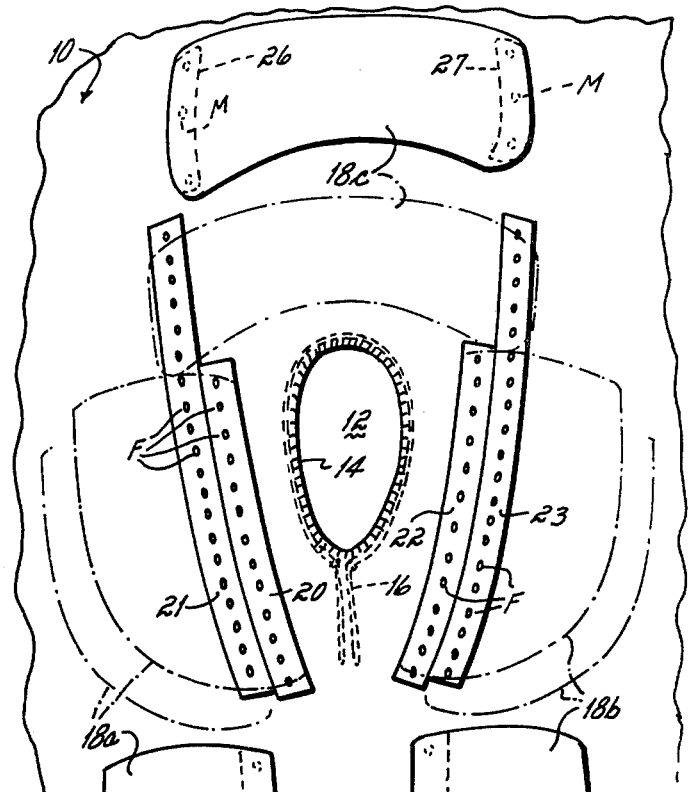
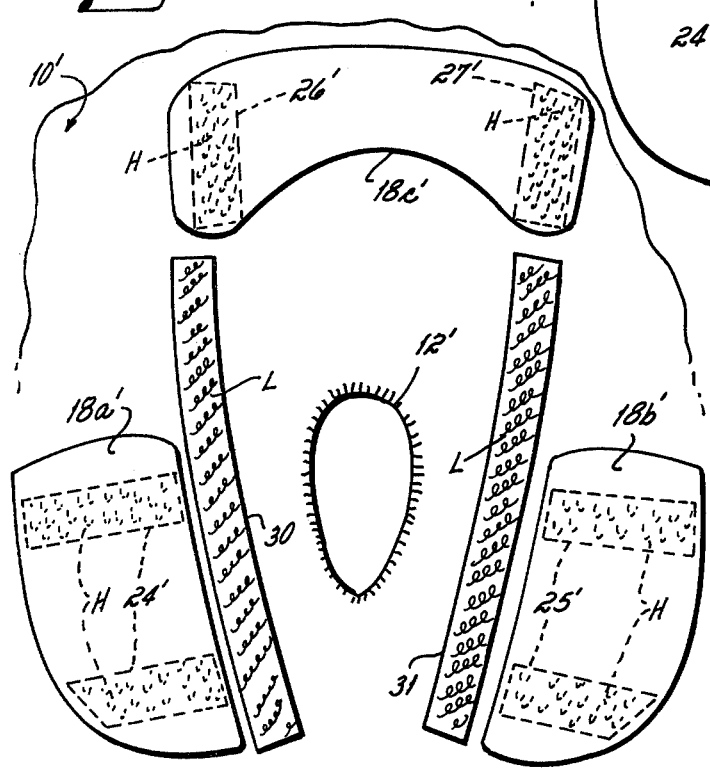
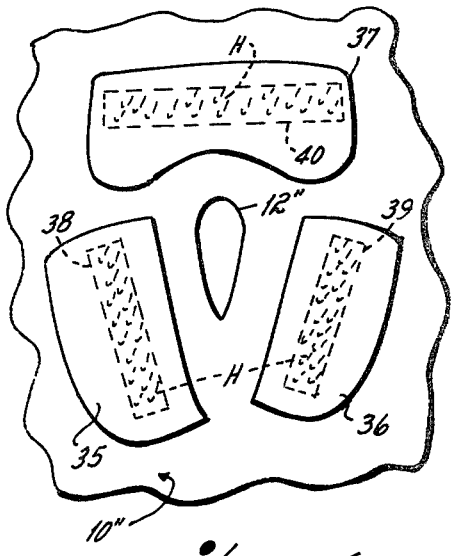

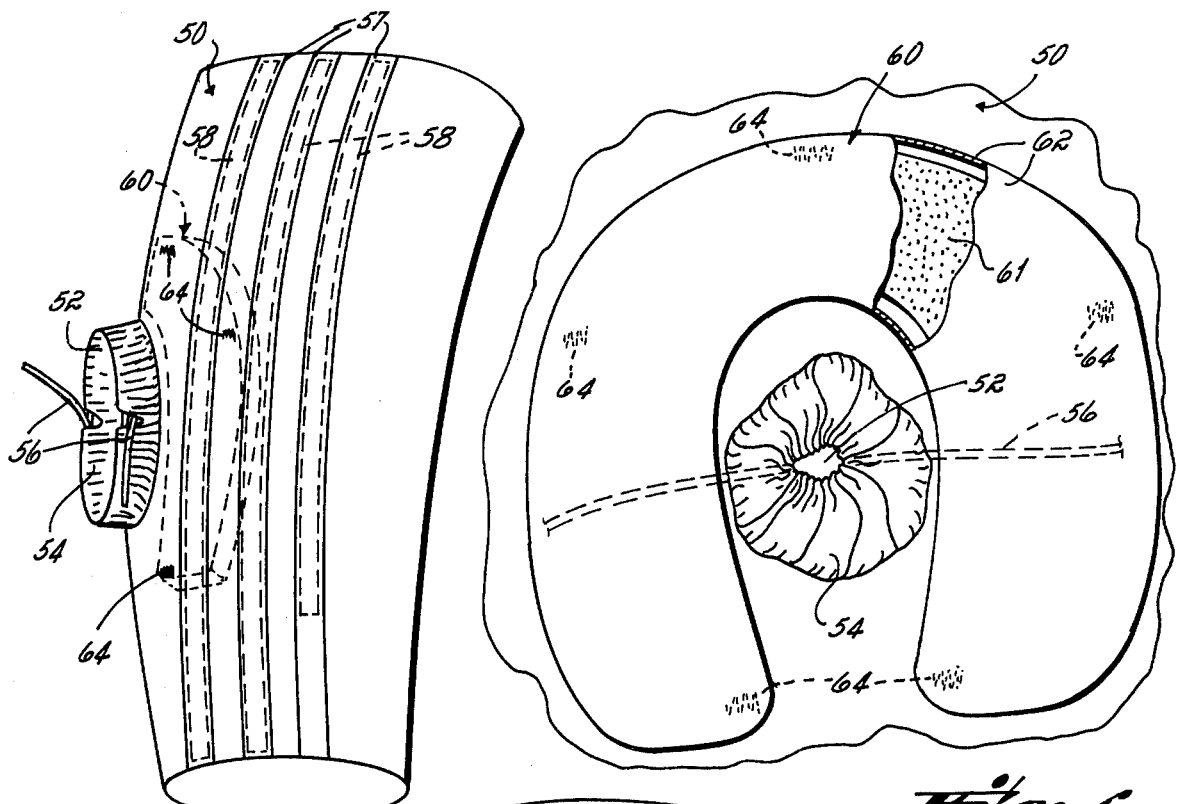
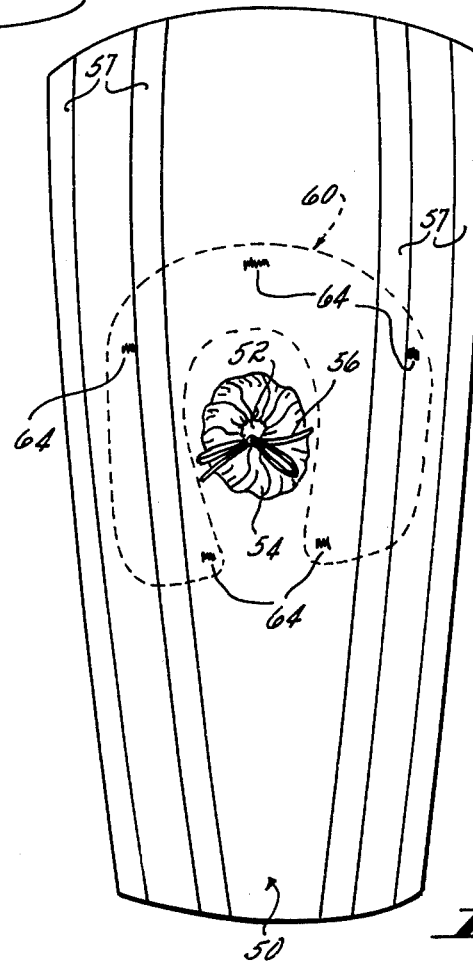

KNEE BRACE

This invention relates to knee braces, and more particularly to knee braces of the type having an elastic sleeve with an opening in the front central portion thereof through which the user's patella projects.

Circumferentially stretchable elastic sleeves which encircle a person's knee to provide inward compressive force thereto have been in use for many years. Typically, the front central portion of the sleeve is provided with an opening of fixed configuration through which the user's patella projects. Lateral pads located on opposite sides of the fixed opening are often secured to the interior of the sleeve to provide additional protection for the user's knee in the region flanking the patella.

A disadvantage of elastic sleeves having fixed configuration patella openings is that optimal fit, comfort and protection can be obtained only by an individual having a patella identically configured to the fixed configuration patella opening provided in the sleeve. If the user's patella is smaller than the opening provided therefor, the periphery of the user's patella is not snugly embraced by the opening to lock the sleeve in the desired vertical position about the knee. As a consequence, the sleeve can ride vertically up or down on the user's leg when the knee is bent. In addition to being uncomfortable, this causes the location of the protective pads of the brace flanking the patella opening to shift relative to the patella, thereby reducing the protection and support provided by the pads when the knee is flexed. If the patella is too large relative to the opening in the sleeve, the patella does not project through it. This also gives rise to vertical shifting of the sleeve when the knee is flexed and the attendant discomfort and shifting of the protective pads from the location of optimal support and protection adjacent the patella.

Accordingly, it has been an objective of this invention to provide a knee brace which can accommodate differently sized and/or configured patellas. This objective has been accomplished in accordance with certain of the principles of this invention by securing to the margin of the patella opening a hollow casing in which is slidably positioned a drawstring for adjustably varying the circumference of the opening. The adjustment capability provided by the drawstring permits the patella opening to be varied, either enlarged or reduced, as is necessary to snugly embrace the periphery of the user's patella regardless of the size and/or shape of the patella of the particular user. Thus, a knee brace is provided having a patella opening which can provide optimal fit, comfort and protection for different individuals having differently sized and/or configured patellas.

In accordance with a further aspect of the invention, the drawstring is fabricated of substantially inelastic material. In this way, once the circumference of the patella opening is adjusted to snugly embrace the periphery of the user's patella, the opening does not enlarge when the knee is flexed and the portions of the elastic sleeve around the patella opening stretch in a horizontal and/or vertical direction. By maintaining the opening at a fixed circumference when the knee is flexed, protective pads secured to the interior of the sleeve proximate the opening do not shift rearwardly as would otherwise tend to occur, but rather remain at their desired position proximate the opening to maintain the protection and support provided by the pads notwithstanding knee flexure.

In accordance with a still further aspect of the invention, the hollow casing secured to the margin of the opening in which the drawstring is slidable to vary the circumference of the opening, is fabricated of two-way stretch material. Such a construction avoids puckering, which is uncomfortable and unattractive, when the drawstring is tightened to reduce the circumference of the opening.

In accordance with another and equally important aspect of the invention adjustable fasteners between the interior of the sleeve and the pads are provided. This permits the pads to be moved toward or away from the kneecap opening as the circumference thereof is decreased and increased by the drawstring to accommodate small and large patellas. This further enhances the comfort and support provided by the brace.

In accordance with another important aspect of this invention the protective pads are mounted to the interior of the elastic sleeve by securing male Velcro strips to the pads, and directly engaging the hooks projecting from the male Velcro strips and the interior surface of the elastic sleeve, which sleeve is fabricated of an open knit type elastic fabric to facilitate secure engagement between the threads of the elastic sleeve and the projecting hooks of the male Velcro fasteners secured to the pads. This method of securing the pads to the interior of the sleeve eliminates the cost (materials and labor) of providing Velcro strips on the interior of the sleeve which cooperate with the Velcro strips on the pads. In addition, and since the Velcro strips are not themselves elastic, by eliminating the need to attach Velcro strips to the interior of the elastic sleeve, the elasticity of the sleeve is not reduced as would otherwise occur were inelastic Velcro strips secured, by stitching or otherwise, to the interior of the elastic sleeve.

These and other advantages and objectives of the invention will become more readily apparent from a detailed description thereof taken in conjunction with drawings in which:

FIG. 1 is a perspective view of one preferred embodiment of the knee brace of this invention;

FIG. 2 is an exploded view of a portion of the interior of the knee brace of FIG. 1, showing the orientation of the pads relative to the patella opening of the knee brace;

FIG. 3 is an elevational view of the interior of the front of a second embodiment of the invention showing the pads secured to the interior of the sleeve using cooperating male and female Velcro strips having interengaging hooks and loops, respectively;

FIG. 4 is an elevational view of the interior of the front of a third embodiment of the invention showing the pads secured to the interior of the sleeve by direct engagement between the sleeve fabric and hook elements projecting from the male Velcro strips secured to the pads;

FIG. 5 is a perspective view of a fourth embodiment of the invention showing a knee brace having an adjustable patella opening and a floating horseshoe-shaped pad secured to the interior thereof;

FIG. 6 is an elevational view of a portion of the interior of the front of the knee brace of FIG. 5, showing the floating mounting arrangement for the pad; and FIG. 7 is a front elevational view of the front of the brace shown in FIGS. 5 and 6.

With reference to FIGS. 1 and 2, one preferred embodiment of the invention is seen to include a tubular sleeve 10 which is adapted to encircle the knee region of the user and extend, when worn, between points located above the knee and below the knee. In practice, a length measured in the vertical direction of approximately eleven inches has been found satisfactory for knee braces designed to be worn by adults. Of course, the vertical length can be varied as desired, and forms no part of this invention. The circumference, or girth, of the sleeve 10 is designed to snugly embrace the user's knee region and apply inward compressive forces thereto when placed in encircling relationship about the user's knee. To this end, the sleeve 10 is fabricated of material which is stretchable in at least a leg-encircling or circumferential direction; in certain cases it may be desirable to construct the sleeve 10 of material which is also stretchable in a vertical direction.

Located in the front of the sleeve 10, approximately midway between the upper and lower edges thereof, is an opening 12 through which the user's patella projects when the brace is properly positioned about the wearer's knee region.

Secured to the inside of the sleeve 10 are a pair of lateral resilient pads 18a and 18b disposed on opposite sides of the patella opening 12, and an upper resilient pad 18c disposed above the patella opening. In practice, the lateral pads 18a and 18b and the upper pad 18c are designed to provide protection and support to the knee at points immediately adjacent or proximate, each side and above the patella.

To facilitate adjusting the lateral pads 18a and 18b toward and away from the patella opening 12, as the circumference of the opening is varied in a manner to be described to accommodate different sized patellas, adjustable securing means are provided. In one preferred form a pair of vertically disposed inelastic strips, 20,21 and 22,23 are sewn or otherwise secured to the sleeve 10 on each side of the patella opening 12. The inelastic strips 20–23 are each provided with a series of vertically spaced female gripping elements F, . . . F which are designed to cooperate with male gripping elements M, . . . M projecting from cooperating inelastic strips 24 and 25 sewn or otherwise secured to the pads 18a and 18b.

For large patellas, the strips 24 and 25 on pads 18a and 18b can be mounted to the outer strips 21 and 23 on the sleeve interior by engagement of the male elements M, . . . M and the female elements F, . . . F of the respective strips. Similarly, and for small patellas, the strips 24 and 25 on pads 18a and 18b can be secured to the inner strips 20 and 22 on the interior of the sleeve 10.

In a similar fashion the vertical position of the upper pad 18c can be moved toward or away from the center of the opening 12. Specifically, strips 26 and 27 on pad 18c having projecting male fastening elements M, . . . M are secured to the opposite vertical edges of the pads 18c. The strips 26 and 27 cooperate with the upper portions of the strips 21 and 23. By engaging the male fasteners M, . . . M of strips 26 and 27 secured to pad 18c with different ones of the female elements F, . . . F of the upper portion of strips 21 and 23, the pad 18c can be located at different vertical positions relative to the center of the patella opening 12 to accommodate differently sized patellas.

Connected to the marginal portion of the opening 12 is a hollow casing 14 which extends around, and is stitched to, substantially the entire margin of the opening. Located within the casing 14 and slidable relative thereto is an adjustable circumference ring, or drawstring 16, which can be tied at varying points along its length to adjust the circumference of opening 12. The casing 14 is preferably constructed of two-way stretch elastic material to avoid puckering when the circumference of the opening 12 established by the drawstring 16 is varied depending on the size of the wearer's patella.

The drawstring 16 is preferably made of material which is substantially inelastic so that once adjusted to a particular circumference to accommodate a particular user's patella the circumference of opening 12 will not change when the knee is subsequently flexed, as would otherwise tend to occur upon knee flexure when portions of the sleeve contiguous to the opening 12 stretch. As noted, as a consequence of the inelastic nature of the drawstring 16, once the circumference of the opening 12 is adjusted such that the margin of the opening 12 snugly embraces the user's patella, when the knee is thereafter flexed the circumference of the opening 12 remains virtually unchanged. This, in turn, prevents those portions of the elastic sleeve 10 contiguous with the opening 12 from moving rearwardly away from the patella when the knee is flexed. With those portions of the sleeve 10 contiguous with the opening 12 remaining proximate the patella opening when the knee is flexed, pads 18a, 18b and 18c secured to the interior of the sleeve flanking opposite sides and the top of the patella will not move rearwardly when the knee is flexed. Since the position of the pads 18a, 18b and 18c relative to the knee region on opposite sides and above the patella does not change when the knee is flexed, the protection and support provided by the pads do not change as the knee is varied between straightened and flexed conditions.

The inelastic drawstring 16, in addition to accommodating different sized patellas, also enhances the comfort of the sleeve. Specifically, the opening 12 can be customized to snugly embrace the patella periphery of individuals having differently sized and/or shaped patellas. Thus, the sleeve 10 can be used by people having varying sized and/or shaped patellas without having to make permanent structural modifications in the sleeve for each different individual.

When the drawstring 16 is adjusted such that the marginal portions of the sleeve 10 defining the opening 12 snugly embrace the periphery of the user's patella, the patella fully projects through the opening 12 and effectively locks the sleeve 10 in a generally fixed vertical relationship with respect to the knee, particularly during knee flexure. If the opening 12 is too large in comparison to the user's patella, the locking action, which occurs when the opening 12 is properly sized to snugly embrace the periphery of the user's patella, does not occur and the sleeve 10 is free to move a limited amount vertically relative to the knee joint, particularly when the knee is flexed. This is undesirable because it causes the location of the pads 18a, 18b and 18c to shift vertically upon knee flexure. In addition, if the opening 12 is too large relative to the user's patella, the pads 18a and 18b flanking the opening on either side thereof may be spaced laterally from the peripheral regions of the patella and fail to provide support immediately adjacent the patella periphery where it is desired. If the opening 12 is too small vis-a-vis the user's patella, the patella does not project through the opening 12. This is not only uncomfortable, but is devoid of even limited locking action between the patella and the sleeve opening.

Instead of using the fastening strips 21–23 secured to the interior of the sleeve 10 and cooperating strips 24–27 secured to the pads 18a–18c, which utilize cooperating male and female fasteners M, . . . M and F, . . .

F, male and female Velcro strips may be used as shown in FIG. 3. For example, and as shown in FIG. 3, upper and lower transversely disposed male Velcro strips 24, 24' and 25, 25' having projecting hooks H, . . . H may be substituted for fastening strips 24 and 25 secured to pads 18a and 18b; vertically disposed male Velcro strips 26' and 27' having projecting hooks H, . . . H may be substituted for male fastening strips 26 and 27 secured to pad 18c; and vertically disposed female Velcro strips 30 and 31 having projecting hooks L, . . . L may be substituted for female fastening strips 21-23 secured to the interior of the sleeve 10'.

In the embodiment of FIG. 4, the lateral pads 35 and 36 and upper pad 37 are adjustably positionably secured to the interior of the sleeve 10" using only male Velcro strips 38, 39 and 40 secured to pads 35, 36 and 37. Strips 38, 39 and 40 have projecting hooks H, . . . H which directly engage the threads of the elastic fabric sleeve 10" which, for this purpose, is designed to have an open weave. Thus, in the embodiment of FIG. 4, it is unnecessary to stitch or otherwise secure female Velcro strips to the sleeve 10" for engagement with the male Velcro strips 38, 39 and 40 secured to the pads 35, 36 and 37. This results in improved elasticity of the sleeve 10".

More specifically, and with particular reference to the embodiment shown in FIG. 3 in which female Velcro pads 30 and 31 are stitched to the interior of sleeve 10', it is noted that in those regions of the elastic sleeve 10' underlying the female Velcro strips 30 and 31 which are stitched thereto, the elasticity of the sleeve is lost since the Velcro strips themselves are not elastic. Thus, in the embodiment depicted in the FIG. 3, the elasticity of the sleeve 10' is lost in those areas where superimposed inelastic strips 30 and 31 are stitched thereto. Whereas, and by way of contrast, in the embodiment of FIG. 4 where the male Velcro strips 38, 39 and 40 secured to the pads 35, 36 and 37 have hooks H, . . . H which directly engage the elastic fabric of the sleeve 10", there are no inelastic Velcro strips stitched to the interior of the sleeve 10". Hence, there are no regions of the elastic sleeve 10" which underlie inelastic strips stitched thereto to cause such underlying regions of the sleeve to lose their elasticity.

The embodiment of FIG. 4, in addition to enhancing the elasticity of the sleeve 10", also results in cost reduction. Specifically, by engaging the hooks H, . . . H of the Velcro strips 38, 39 and 40 stitched to pads 35, 36 and 37 directly to the fabric 10", the cost, including material and labor, of providing female Velcro strips stitched or otherwise secured to the interior of the sleeve 10" is eliminated.

A still further advantage of the knee brace depicted in FIGS. 1-4 is that the protective pads can be removed when it is necessary to launder the elastic sleeve. If the brace is laundered by hand (vis-a-vis by machine), it is easier to thoroughly wash the sleeve, particularly the interior thereof, with the pads removed. Drying of the brace following laundering is also more quickly accomplished with the pads removed. If the brace is dried in an electric or gas dryer, removal of the pads during the drying operation is particularly useful where the pads are fabricated of foam rubber which is deleteriously affected by high temperatures often found in laundry drying equipment.

In accordance with a still further embodiment of the invention depicted in FIGS. 5, 6 and 7, a knee brace is provided having an elastic sleeve 50 constructed similarly to the elastic sleeves shown in the embodiments of FIGS. 1-4. The sleeve 50 is provided with a patella opening 52 having secured to the margin thereof a two-way stretch elastic casing 54 within which is slidably positioned a drawstring 56. The opening 52, casing 54 and drawstring 56 have the same structure, function and advantages in the embodiments shown in FIGS. 5-7 as these elements have in the embodiments shown in FIGS. 1-4.

Secured to the exterior of the elastic sleeve 50 on either side of the patella opening 52 are a plurality of pocket-forming elongated vertically disposed strips 57, . . . 57. Disposed within the pocket defined by the strips 57, . . . 57 are stays 58, . . . 58. The length of at least one of the stays 58 is substantially coextensive with the vertical dimension of the sleeve 50 to prevent the upper and lower edges of the sleeve from curling up and reducing the effective length of the sleeve.

Located in the interior of the sleeve 50 is a horseshoe-shaped pad assembly 60. The pad assembly 60 includes a horseshoe-shaped pad 61 of resilient material which has an elasticity in the circumferential direction which is substantially less than the circumferential elasticity of the sleeve 50. The horseshoe-shaped pad 61 is enclosed within a fabric casing 62 of two-way stretch material. The casing 62 is secured to the interior of the sleeve 50 at points 64 along its outer periphery which are substantially spaced from each other by suitable means such as stitching. By securing the pad assembly 60 to the interior of the sleeve at intermittent points along the outer periphery of the pad assembly, a "floating" mounting arrangement for the pad assembly relative to the patella opening 52 is provided. This enhances the comfort and fit of the brace by allowing limited relative movement of the pad 61 relative to the sleeve 50 as may be necessary to accommodate the knees of individuals having differently configured patellas.

What is claimed is:

1. A knee brace comprising:

a one-piece tubular sleeve exhibiting substantial circumferential elasticity in a knee-encircling direction and configured to encircle the leg of a user in the region extending between points above and below the knee, said sleeve having a circumference when unstretched which is less than the girth of a user's leg in the region of the knee to apply inwardly directed compressive force to the user's knee region when encircled thereabout, said sleeve having an opening therein defined by a peripheral margin to permit projection of the user's patella therethrough when said sleeve encircles said user's knee region, a substantially inelastic flexible drawstring ring connected to and coextensive with said margin to prevent enlargement of said patella opening and to maintain snug engagement between said opening and the periphery of a user's patella projecting therethrough when the user's knee joint is flexed and said elastic sleeve stretched, said inelastic flexible drawstring ring being adjustable in circumference to facilitate drawing said margin of said patella opening snugly around the periphery of different sized patellas, and a guide secured to said peripheral margin, said inelastic flexible drawstring ring slidingly engaged by said guide to facilitate relative motion therebetween to permit adjusting the circumference of said patella opening to snugly embrace the periphery of differently configured patellas.

2. A knee brace of claim 1 wherein said guide includes a hollow casing secured to said margin, said drawstring being slidable within said casing, said casing being fabricated of two-way stretch material to avoid puckering when said drawstring is tightened to reduce the circumference of said patella opening.

3. The knee brace of claims 1 or 2 further including at least one pad secured to the interior of said sleeve adjacent the patella opening, said pad being maintained adjacent the periphery of the patella of a user when the knee is flexed by reason of the maintenance of said snug engagement between said peripheral margin of said opening and said patella periphery during knee flexure.

4. The knee brace of claims 1 or 2 further including at least one pad, and means for selectively adjustably securing said pad to the interior of said sleeve at different locations thereof to facilitate placement of said pad adjacent said patella opening notwithstanding variations in circumference of said patella opening occasioned by variations in size of patellas which are snugly embraced by said adjustably sized patella opening.

5. The knee brace of claims 1 or 2 further including at least one pad and a Velcro strip secured to said pad having hooks projecting therefrom, said sleeve being constructed on the interior surface thereof proximate said patella opening of open weave elastic fabric which is exposed to facilitate direct engagement between the threads thereof and said hooks projecting from said Velcro strip secured to said pad.

6. A knee brace comprising:
a one-piece tubular sleeve exhibiting substantial circumferential elasticity in a knee-encircling direction and configured to encircle the leg of a user in the region extending between points above and below the knee, said sleeve having a circumference when unstretched which is less than the girth of a user's leg in the region of the knee to apply inwardly directed compressive force to the user's knee region when encircled thereabout,
said sleeve having an opening therein defined by a peripheral margin to permit projection of the user's patella therethrough when said sleeve encircles said user's knee region,
a guide secured to said peripheral margin, and
an adjustable flexible drawstring ring connected to and coextensive with said margin and engaged with said guide to facilitate drawing said margin of said opening snugly around the periphery of differently sized patellas.

7. The knee brace of claim 6 wherein said guide includes a hollow casing secured to said margin, said drawstring being slidable within said casing, said casing being fabricated of two-way stretch material to avoid puckering when said drawstring is tightened to reduce the circumference of said patella opening.

8. The knee brace of claims 6 or 7 further including at least one pad, and means for selectively adjustably securing said pad to the interior of said sleeve at different locations thereof to facilitate placement of said pad adjacent said patella opening notwithstanding variations in circumference of said patella opening occasioned by variations in size of patellas which are snugly embraced by said adjustably sized patella opening.

9. The knee brace of claims 6 or 7 further including at least one pad and a Velcro strip secured to said pad having hooks projecting therefrom, said sleeve being constructed on the interior surface thereof proximate said patella opening of open weave elastic fabric which is exposed to facilitate direct engagement between the threads thereof and said hooks projecting from said Velcro strip secured to said pad.

10. A knee brace comprising:
a one-piece tubular sleeve exhibiting substantial circumferential elasticity in a knee-encircling direction and configured to encircle the leg of the user in the region extending between points above and below the knee, said sleeve having a circumference when unstretched which is less than the girth of a user's leg in the region of the knee to apply inwardly directed compressive force to the user's knee region when encircled thereabout,
said sleeve having an opening therein defined by a physically continuous peripheral margin to permit projection of the user's patella therethrough when said sleeve encircles said user's knee region,
a physically continuous adjustable ring connected to and coextensive with said margin to facilitate drawing said margin of said opening snugly around the periphery of differently sized patellas,
said physically continuous margin and ring facilitating adjustment of the size and/or configuration of said patella opening independently of the circumference of said sleeve when unstretched.

11. A knee brace comprising:
a one-piece tubular sleeve exhibiting substantial circumferential elasticity in a knee-encircling direction and configured to encircle the leg of a user in the region extending between points above and below the knee, said sleeve having a circumference when unstretched which is less than the girth of a user's leg in the region of the knee to apply inwardly directed compressive force to the user's knee region when encircled thereabout,
said sleeve having an opening therein defined by a physically continuous peripheral margin to permit projection of the user's patella therethrough when said sleeve encircles said user's knee region,
a physically continuous substantially inelastic ring connected to and coextensive with said margin to prevent enlargement of said patella opening and to maintain snug engagement between said opening and the periphery of a user's patella projecting therethrough when the user's knee joint is flexed and said elastic sleeve stretched, said physically continuous margin and ring rendering the size and/or configuration of said opening independent of the circumference of said sleeve when unstretched.

12. The knee brace of claim 11 wherein said inelastic ring is adjustable in circumference to facilitate drawing said margin of said patella opening snugly around the periphery of different sized patellas.

13. The knee brace of claims 6, 7, 11 or 12 further including at least one pad secured to the interior of said sleeve adjacent the patella opening, said pad being maintained adjacent the periphery of the patella of a user when the knee is flexed by reason of the maintenance of said snug engagement between said peripheral margin of said opening and said patella periphery during knee flexure.

* * * * *